US007030129B2

(12) United States Patent
Miller et al.

(10) Patent No.: US 7,030,129 B2
(45) Date of Patent: Apr. 18, 2006

(54) METHOD OF REDUCING AND TREATING UVB-INDUCED IMMUNOSUPPRESSION

(75) Inventors: Richard L. Miller, Maplewood, MN (US); Anthony A. Gaspari, Cockeysville, MD (US); Joseph A. Gillis, Eagan, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 137 days.

(21) Appl. No.: 10/371,146

(22) Filed: Feb. 20, 2003

(65) Prior Publication Data

US 2003/0161797 A1 Aug. 28, 2003

Related U.S. Application Data

(60) Provisional application No. 60/358,982, filed on Feb. 22, 2002.

(51) Int. Cl.
*A61K 31/52* (2006.01)
*A61K 31/505* (2006.01)

(52) U.S. Cl. ............ 514/262; 514/256; 514/291; 514/292

(58) Field of Classification Search ........ 514/291, 514/292, 885, 262, 256
See application file for complete search history.

(56) References Cited

U.S. PATENT DOCUMENTS

| | | | |
|---|---|---|---|
| 4,689,338 A | 8/1987 | Gerster | |
| 4,698,348 A | 10/1987 | Gerster | |
| 4,929,624 A | 5/1990 | Gerster et al. | |
| 4,988,815 A | 1/1991 | Andre et al. | |
| 5,037,986 A | 8/1991 | Gerster | |
| 5,175,296 A | 12/1992 | Gerster | |
| 5,238,944 A | 8/1993 | Wick et al. | |
| 5,266,575 A | 11/1993 | Gerster | |
| 5,268,376 A | 12/1993 | Gester | |
| 5,346,905 A | 9/1994 | Gerster | |
| 5,352,784 A | 10/1994 | Nikolaides et al. | |
| 5,367,076 A | 11/1994 | Gerster | |
| 5,376,501 A | 12/1994 | Mariën et al. | |
| 5,389,640 A | 2/1995 | Gerster et al. | |
| 5,395,937 A | 3/1995 | Nikolaides et al. | |
| 5,446,153 A | 8/1995 | Lindstrom et al. | 544/127 |
| 5,482,936 A | 1/1996 | Lindstrom | |
| 5,494,916 A | 2/1996 | Lindstrom et al. | |
| 5,525,612 A | 6/1996 | Gerster | |
| 5,605,899 A | 2/1997 | Gerster et al. | |
| 5,693,811 A | 12/1997 | Lindstrom | |
| 5,741,908 A | 4/1998 | Gerster et al. | |
| 5,756,747 A | 5/1998 | Gerster et al. | |
| 5,840,732 A * | 11/1998 | Takatani et al. | 514/300 |
| 5,939,090 A | 8/1999 | Beaurline et al. | |
| 6,028,076 A | 2/2000 | Hirota et al. | |
| 6,028,097 A | 2/2000 | Okuhara et al. | 514/411 |
| 6,039,969 A | 3/2000 | Tomai et al. | |
| 6,069,149 A | 5/2000 | Nanba et al. | |
| 6,083,505 A | 7/2000 | Miller et al. | |
| 6,110,929 A | 8/2000 | Gerster et al. | |
| 6,113,918 A | 9/2000 | Johnson et al. | |
| 6,194,338 B1 | 2/2001 | Andolfatto et al. | |
| 6,194,425 B1 | 2/2001 | Gerster et al. | |
| 6,200,592 B1 * | 3/2001 | Tomai et al. | 424/434 |
| 6,207,646 B1 | 3/2001 | Krieg et al. | |
| 6,239,116 B1 | 5/2001 | Krieg et al. | |
| 6,245,776 B1 | 6/2001 | Skwierczynski et al. | |
| 6,303,347 B1 | 10/2001 | Johnson et al. | |
| 6,329,381 B1 | 12/2001 | Kurimoto et al. | |
| 6,331,539 B1 | 12/2001 | Crooks et al. | |
| 6,339,068 B1 | 1/2002 | Krieg et al. | |
| 6,376,501 B1 | 4/2002 | Isobe et al. | 514/262 |
| 6,376,669 B1 | 4/2002 | Rice et al. | |
| 6,387,938 B1 | 5/2002 | Mizuguchi et al. | 514/394 |
| 6,406,705 B1 | 6/2002 | Davis et al. | |
| 6,426,334 B1 | 7/2002 | Agrawal et al. | |
| 6,451,810 B1 | 9/2002 | Coleman et al. | |
| 6,455,032 B1 | 9/2002 | Kelly et al. | |
| 6,476,000 B1 | 11/2002 | Agrawal | |
| 6,518,265 B1 | 2/2003 | Kato et al. | 514/228.5 |
| 6,525,028 B1 | 2/2003 | Johnson et al. | |
| 6,525,064 B1 | 2/2003 | Dellaria et al. | |
| 6,541,485 B1 | 4/2003 | Crooks et al. | |
| 6,545,016 B1 | 4/2003 | Dellaria et al. | 514/303 |
| 6,545,017 B1 | 4/2003 | Dellaria et al. | 514/303 |
| 6,558,951 B1 * | 5/2003 | Tomai et al. | 435/337 |
| 6,573,273 B1 | 6/2003 | Crooks et al. | 514/293 |
| 6,649,172 B1 | 11/2003 | Johnson | |
| 6,656,938 B1 | 12/2003 | Crooks et al. | |
| 6,660,735 B1 | 12/2003 | Crooks et al. | |
| 6,660,747 B1 | 12/2003 | Crooks et al. | |
| 6,664,260 B1 | 12/2003 | Charles et al. | |
| 6,664,264 B1 | 12/2003 | Dellaria et al. | |

(Continued)

FOREIGN PATENT DOCUMENTS

EP     0 394 026     10/1990

(Continued)

OTHER PUBLICATIONS

Racchkova et al., Database Caplus (AN 2000:109451), Free radical production, immunosuppression . . . , (abstract only), Periodicum Biologorum, 1999, vol. 101(3), pp. 187-192.*

(Continued)

*Primary Examiner*—Vickie Kim
(74) *Attorney, Agent, or Firm*—Christopher D. Gram; Ted K. Ringsred; Robert W. Sprague (57) ABSTRACT

Methods of preventing and/or treating UV-induced immunosuppression by administration of immune response modifier compounds are disclosed herein. Suitable immune response modifier compounds include agonists of one or more TLRs.

16 Claims, 4 Drawing Sheets

U.S. PATENT DOCUMENTS

| | | |
|---|---|---|
| 6,664,265 B1 | 12/2003 | Crooks et al. |
| 6,667,312 B1 | 12/2003 | Bonk et al. |
| 6,670,372 B1 | 12/2003 | Charles et al. |
| 6,677,347 B1 | 1/2004 | Crooks et al. |
| 6,677,348 B1 | 1/2004 | Heppner et al. |
| 6,677,349 B1 | 1/2004 | Griesgraber |
| 6,683,088 B1 | 1/2004 | Crooks et al. |
| 6,706,728 B1 | 3/2004 | Hedenstrom et al. |
| 6,743,920 B1 | 6/2004 | Lindstrom et al. |
| 6,756,382 B1 | 6/2004 | Coleman et al. |
| 6,790,434 B1 * | 9/2004 | Borchert et al. .............. 424/59 |
| 6,818,650 B1 | 11/2004 | Griesgraber |
| 2002/0016332 A1 | 2/2002 | Slade |
| 2002/0055517 A1 | 5/2002 | Smith |
| 2002/0058674 A1 | 5/2002 | Hedenstrom et al. |
| 2002/0110840 A1 | 8/2002 | Tomai et al. |
| 2003/0022302 A1 | 1/2003 | Lewis et al. |
| 2003/0113733 A1 * | 6/2003 | Khan et al. ................. 435/6 |
| 2003/0129605 A1 * | 7/2003 | Yu et al. ..................... 435/6 |
| 2003/0130299 A1 | 7/2003 | Crooks et al. |
| 2003/0133913 A1 | 7/2003 | Tomai et al. |
| 2003/0134283 A1 * | 7/2003 | Peterson et al. ............... 435/6 |
| 2003/0139364 A1 * | 7/2003 | Krieg et al. ................... 514/44 |
| 2003/0144283 A1 | 7/2003 | Coleman et al. |
| 2003/0161797 A1 | 8/2003 | Miller et al. |
| 2003/0198609 A1 * | 10/2003 | Bunger ....................... 424/59 |
| 2003/0199461 A1 | 10/2003 | Averett et al. |
| 2003/0199538 A1 * | 10/2003 | Skwierczynski et al. .... 514/291 |
| 2004/0010007 A1 | 1/2004 | Dellaria et al. |
| 2004/0014779 A1 | 1/2004 | Gorden et al. |
| 2004/0023870 A1 | 2/2004 | Dedera et al. |
| 2004/0091491 A1 | 5/2004 | Kedl et al. |
| 2004/0132079 A1 | 7/2004 | Gupta et al. |
| 2004/0141950 A1 | 7/2004 | Noelle et al. |
| 2004/0147543 A1 | 7/2004 | Hays et al. |
| 2004/0162309 A1 | 8/2004 | Gorden et al. |
| 2004/0171086 A1 | 9/2004 | Fink et al. |
| 2004/0175336 A1 | 9/2004 | Egging et al. |
| 2004/0176367 A1 | 9/2004 | Griesgraber et al. |
| 2004/0180919 A1 | 9/2004 | Miller et al. |
| 2004/0181130 A1 | 9/2004 | Miller et al. |
| 2004/0181211 A1 | 9/2004 | Graham et al. |
| 2004/0191833 A1 | 9/2004 | Fink et al. |
| 2004/0192585 A1 | 9/2004 | Owens et al. |
| 2004/0202720 A1 | 10/2004 | Wightman et al. |
| 2004/0214851 A1 | 10/2004 | Birmachu et al. |

FOREIGN PATENT DOCUMENTS

| | | |
|---|---|---|
| EP | 1 104 764 | 6/2001 |
| JP | 9-208584 | 8/1997 |
| JP | 9-255926 | 3/1999 |
| JP | 11-80156 | 3/1999 |
| JP | 11-222432 | 8/1999 |
| JP | 2000-247884 | 9/2000 |
| WO | WO 00/47719 | 8/2000 |
| WO | WO 00/75304 A1 | 12/2000 |
| WO | WO 00/76505 | 12/2000 |
| WO | WO 00/76518 | 12/2000 |
| WO | WO 01/72287 A2 | 10/2001 |
| WO | WO 01/74343 | 10/2001 |
| WO | WO 01/74343 A2 | 10/2001 |
| WO | WO 02/36592 | 5/2002 |
| WO | WO 02/36592 A1 | 5/2002 |
| WO | WO 02/46188 | 6/2002 |
| WO | WO 02/46188 A2 | 6/2002 |
| WO | WO 02/46189 | 6/2002 |
| WO | WO 02/46189 A2 | 6/2002 |
| WO | WO 02/46190 | 6/2002 |
| WO | WO 02/46190 A2 | 6/2002 |
| WO | WO 02/46191 | 6/2002 |
| WO | WO 02/46191 A2 | 6/2002 |
| WO | WO 02/46192 | 6/2002 |
| WO | WO 02/46192 A2 | 6/2002 |
| WO | WO 02/46193 | 6/2002 |
| WO | WO 02/46193 A2 | 6/2002 |
| WO | WO 02/46194 | 6/2002 |
| WO | WO 02/46194 A2 | 6/2002 |
| WO | WO 02/46749 | 6/2002 |
| WO | WO 02/46749 A2 | 6/2002 |
| WO | WO 02/085905 A1 | 10/2002 |
| WO | WO 02/102377 | 12/2002 |
| WO | WO 03/020889 A2 | 3/2003 |
| WO | WO 03/043572 A2 | 5/2003 |
| WO | WO 03/045391 A1 | 6/2003 |
| WO | WO 03/089602 | 10/2003 |
| WO | WO 03/097641 A2 | 11/2003 |
| WO | WO 04/053057 A2 | 6/2004 |

OTHER PUBLICATIONS

Weichenthal et al., Database Caplus (AN 2000:627115), Effects of whole-body UVB irradiation on cytokine . . . , (abstract on;y), 2000, vol. 292(7), pp. 348-353.*

TLR level 5- Initial Investigation , Jun. 10, 2003, NOrth American electric reliability council.*

TLR infection sheet, Definition.*

Twin lens reflex medium format cameras by Robert Monaghan.*

Rachkova et al, Free radiacal production, immunosuppression . . . ,Periodicum biologorum, 1999, vol. 101/3, pp. 187-192.*

Testerman, et al., "Cytokine Induction by the Immunomodulators Imiquimod and S-27609", *Journal of Leukocyte Biology*, vol. 58, pp. 365-375, Sep. 1995.

Chollet, et al, "Development of a Topically Active Imiquimod Formulation", *Pharmaceutical Development and Technology*, 4(1), pp. 34-43 (1999).

Beissert et al., "Mechanisms Involved in Ultraviolet Light-Induced Immunosuppression", *Journal of Investigative Dermatology Symposium Proceedings*, 4:61-64, 1999.

Shen et al., "Modulation of IL-10, IL-12, and IFN-γ in the Epidermis of Hairless Mice by UVA (320-400 nm) and UVB (280-320 nm) Radiation", *J. Invest Dermatol*, 113:1059-1064, 1999.

Nickoloff et al., "Life and Death Signaling in Epidermis: Following a Planned Cell Death Pathway Involving a Trail That Does Not Lead to Skin Cancer", *The Journal of Investigative Dermatologyl*, :1-2, 2001.

Bachmann et al., "Ultraviolet Light Downregulates CD95 Ligand and Trail Receptor Expression Facilitating Actinic Keratosis and Squamous Cell Carcinoma Formation", *J. Invest Dermatol*, 117:59-66, 2001.

Schacker et al., "Imiquimod 5-Percent Cream Does Not Alter the Natural History of Recurrent Herpes Genitalis: a Phase II, Randomized, Double-Blind, Placebo-Controlled Study", *Antimicrobial Agents and Chemotherapy*, 46(10): 3243-3248, Oct. 2002.

130:308468 HCA: Garssen et al., "The role of urocanic acid in UVB-induced suppression of immunity to Trichinella spiralis infection in the rat", *Immunology*, 96(2):298-306, 1999.

Vasilakos, J. P. et al., "Adjuvant Activities of Immune Response Modifier R-848: Comparison with CpG ODN". *Cellular Immunology*. 2000, vol. 204, pp. 64-74.

Wagner, T. L. et al., "Modulation of TH1 and TH2 Cytokine Production with the Immune Response Modifiers, R-848 and Imiquimod". *Cellular Immunology*. 1999, vol. 191, pp. 10-19.

Heil et al.; "Synthetic immunostimulatory compounds activate immune cells via TLR7 and TLR8"; 33th Annual Meeting of the Deutsche Gessellschaft für Immunologie, Marburg 2002—Abstract C.6.

Akira S. et al., "Recognition of pathogen-associated molecular patterns by TLR family", *Immunology Letters*, 2003, vol. 85, pp. 85-95.

Ozinsky A. et al., "The repertoire for pattern recognition of pathogens by the innate immune system is defined by cooperation between Toll-like receptors", *Proc. Nat. Acad. Sci.*. Dec. 2000, vol. 97, No. 25, pp. 13766-13771.

Gorden et al., "Synthetic TLR Agonists Reveal Functional Differences between Human TLR7 and TLR8", *The Journal of Immunology*, 2005, vol. 174, pp. 1259-1268.

Sauder et al., "Randomized, Single-Blind, Placebo-Controlled Study of Topical Application of the Immune Response Modulator Resiquimod in Healthy Adults", *Antimicrobial Agents and Chemotherapy*, Dec. 2003, vol. 47, No. 12, pp. 3846-3852.

Brassard et al.; "Interferon-α as an immunotherapeutic protein"; Journal of Leukocyte Biology; vol. 71, Apr. 2002 pps. 565-581.

Izumi et al.; "1*H*-Imidazo[4,5-*c*]quinoline Derivatives as Novel Potent TNF-α Suppressors: Synthesis and Structure-Activity Relationship of 1-, 2-and 4-Substitued 1*H*-imidazo[4,5-*c*]quinolines or 1*H*-imidazo[4,5-c]pyridines"; Bioorganic & Medicinal Chemistry; 11; 2003; pps. 2541-2550.

Hornung et al., "Quantitative Expression of Toll-Like Receptor 1-10 mRNA in Cellular Subsets of Human Peripheral Blood Mononuclear Cells and Sensitivity to CpG Oligodeoxynucleotides[1]", The Journal of Immunology, 2002, 168; pp. 4531-4537.

Hemmi et al., "Small anti-viral compounds activate immune cells *via* the TLR7 MyD88-dependent Signaling pathway", Nature Immunology, vol. 3, No. 2; Feb. 2002; pp. 196-200.

Medzhitov, "Toll-Like Receptors and Innate Immunity", Nature Reviews Immunology, vol. 1; Nov. 2001, pp. 135-145.

Jurk et al. "Human TLR7 and TLR8 independently confer responsiveness to the antiviral compound R-848", Nature Immunology, Jun. 2002, vol. 3, No. 6; p. 1.

Akira et al., "Toll-like receptors: critical proteins linking innate and acquired immunity", Nature Immunology, Aug. 2001, vol. 2, No. 8; pp. 675-6808.

* cited by examiner

METHOD OF REDUCING AND TREATING UVB-INDUCED IMMUNOSUPPRESSION

RELATED APPLICATION DATA

This application claims priority to U.S. Provisional Patent Application Ser. No. 60/358,982, filed Feb. 22, 2002.

BACKGROUND OF THE INVENTION

Human skin is an organ that protects the body from the influences of the external environment. A portion of that protective function is provided by an immune system specific to the skin—the so-called skin immune system—that protects the body from potentially harmful environmental influences including pathogens and transformed skin cells. The skin immune system may provide a localized response known as contact hypersensitivity (CHS), a systemic response known as delayed type hypersensitivity (DTH), or both.

Exposing skin to ultraviolet radiation of the sun, particularly UV-B radiation, may damage certain types of cells involved in the skin immune system. Such damage may at least partially suppress function of the skin immune system and, therefore, may result in UV-induced immunosuppression.

Langerhans cells are dendritic-like elements of the skin immune system that may function to present antigens to Th1-lymphocytes. Langerhans cells may be particularly affected by exposure to UV radiation. Exposure to UV radiation can cause changes in Langerhans cells that may contribute to UV-induced immunosuppression. For example, exposure to UV radiation may impair the ability of Langerhans cells to present antigens.

Cytokines are known to be involved in the development of contact hypersensitivity (CHS) and the suppression of contact hypersensitivity by UV radiation. For example, interleukin (IL)-10 is a cytokine produced by keratinocytes after the keratinocytes are exposed to UV radiation. IL-10 impairs Langerhans cell function and suppresses CHS. Also, IL-12 promotes a Th1-lymphocyte immune response and is involved in the induction of CHS. IL-12 can reduce the immunosuppressive effects of UV radiation. Furthermore, administration of IL-12 prior to UV treatment may counteract UV-induced systemic suppression of delayed type hypersensitivity (DTH).

Ectoin and ectoin derivatives may be used for the prophylaxis or treatment of UV-induced immunosuppression. Such compounds may be incorporated into compositions for topical administration.

SUMMARY OF THE INVENTION

In one aspect, the present invention provides a method of reducing UV-induced immunosuppression that includes administering to a treatment area an immune response modifier compound in an amount effective to inhibit UV-induced immunosuppression.

In certain embodiments, the immune response modifier compound can be an agonist of at least one Toll-like receptor (TLR). For example, in some embodiments, the immune response modifier compound can include an imidazoquinoline amine, an imidazopyridine amine, a 6,7-fused cycloalkylimidazopyridine amine, a 1,2-bridged imidazoquinoline amine, an imidazonaphthyridine amine, an imidazotetrahydronaphthyridine amine, an oxazoloquinoline amine, a thiazoloquinoline amine, an oxazolopyridine amine, a thiazolopyridine amine, an oxazolonaphthyridine amine, or a thiazolonaphthyridine amine. In certain embodiments, the immune response modifier compound is administered via a topical application vehicle such as a cream, a gel, a spray, an ointment, a lotion, a solution, a suspension, an emulsion, a paste, a powder, or an oil.

In another aspect, the present invention provides a method of treating UV-induced immunosuppression that includes administering to a treatment area an immune response modifier compound in an amount effective to inhibit UV-induced immunosuppression. In certain embodiments, the immune response modifier compound can be an agonist of at least one Toll-like receptor (TLR). For example, in some embodiments, the immune response modifier compound can include an imidazoquinoline amine, an imidazopyridine amine, a 6,7-fused cycloalkylimidazopyridine amine, a 1,2-bridged imidazoquinoline amine, an imidazonaphthyridine amine, an imidazotetrahydronaphthyridine amine, an oxazoloquinoline amine, a thiazoloquinoline amine, an oxazolopyridine amine, a thiazolopyridine amine, an oxazolonaphthyridine amine, or a thiazolonaphthyridine amine.

In certain embodiments, the immune response modifier compound is administered via a topical application vehicle such as a cream, a gel, a spray, an ointment, a lotion, a solution, a suspension, an emulsion, a paste, a powder, or an oil.

Various other features and advantages of the present invention should become readily apparent with reference to the following detailed description, examples, claims and appended drawings. In several places throughout the specification, guidance is provided through lists of examples. In each instance, the recited list serves only as a representative group and should not be interpreted as an exclusive list.

DETAILED DESCRIPTION OF ILLUSTRATIVE EMBODIMENTS OF THE INVENTION

Immune response modifiers ("IRMs") include compounds that possess potent immunostimulating activity including but not limited to antiviral and antitumor activity. Certain IRMs effect their immunostimulatory activity by inducing the production and secretion of cytokines such as, e.g., Type I interferons, TNF-$\alpha$, IL-1, IL-6, IL-8, IL-10, IL-12, MIP-1, and MCP-1. Certain IRMs are small organic molecules such as those disclosed in, for example, U.S. Pat. Nos. 4,689,338; 4,929,624; 5,266,575; 5,268,376; 5,352,784; 5,389,640; 5,482,936; 5,494,916; 6,110,929; 6,194,425; 4,988,815; 5,175,296; 5,367,076; 5,395,937; 5,693,811; 5,741,908; 5,238,944; 5,939,090; 6,039,969; 6,083,505; 6,245,776; 6,331,539; and 6,376,669; and PCT Publications WO 00/76505; WO 00/76518; WO 02/46188, WO 02/46189;

WO 02/46190; WO 02/46191; WO 02/46192; WO 02/46193; and WO 02/46194.

Additional small molecule IRMs include purine derivatives (such as those described in U.S. Pat. Nos. 6,376,501 and 6,028,076), small heterocyclic compounds (such as those described in U.S. Pat. No. 6,329,381), and amide derivatives (such as those described in U.S. Pat. No. 6,069,149).

Other IRMs include large biological molecules such as oligonucleotide sequences. Some IRM oligonucleotide sequences contain cytosine-guanine dinucleotides (CpG) and are described, for example, in U.S. Pat. Nos. 6,1994,388; 6,207,646; 6,239,116; 6,339,068; and 6,406,705. Some CpG-containing oligonucleotides can include synthetic immunomodulatory structural motifs such as those described, for example, in U.S. Pat. Nos. 6,426,334 and 6,476,000. Other IRM nucleotide sequences lack CpG and are described, for example, in International Patent Publication No. WO 00/75304.

Certain IRMs can function as Toll-like receptor (TLR) agonists, i.e., their immunomodulating influence is exerted through a TLR-mediated cellular pathway. For example, some small molecule IRMs have been identified as agonists of one or more of TLRs 2, 4, 6, 7, and 8; and CpG has been identified as an agonist of TLR 9. In many cases, activating a TLR-mediated pathway results in gene transcription (e.g., cytokine or co-stimulatory marker expression) by activating NF-κB regardless of the particular TLR that is activated.

Certain IRM compounds may be useful for the treatment of Th2-mediated diseases because they inhibit the Th2 immune response, suppress IL-4/IL-5 cytokine induction and eosinophilia, and enhance Th1 immune response. IRM compounds that act as an agonist of at least one TLR have been shown to be particularly useful in this regard. Some IRM compounds have been found to have pharmacological effects on Langerhans cells as well. Human Langerhans cells are known to be derived from myeloid dendritic cells that express TLR8.

Therefore, the present invention provides for methods of reducing (including preventing) and/or treating UV-induced immunosuppression by administering one or more IRM compounds. In certain embodiments of the present invention, UV-induced immunosuppression may be reduced by prophylactic administration of an IRM compound to a portion of the skin (e.g., topical application) before the skin is exposed to UV radiation. In an alternative embodiment, UV-induced immunosuppression may be therapeutically treated by administration of an IRM compound to a portion of the skin (e.g., topical application) that has already been exposed to UV radiation. In yet other alternative embodiments, prophylactically reducing or therapeutically treating UV-induced immunosuppression may be accomplished by administering one or more IRM compounds systemically.

In certain embodiments, the IRM compound includes an agonist of at least one TLR. In particular embodiments, the IRM compound can be an agonist of TLR7, TLR8, or TLR9. For example, the IRM compound can be an imidazopyridine amine, a 6,7-fused cycloalkylimidazopyridine amine, a 1,2-bridged imidazoquinoline amine, an imidazonaphthyridine amine, an imidazotetrahydronaphthyridine amine, an oxazoloquinoline amine, a thiazoloquinoline amine, an oxazolopyridine amine, a thiazolopyridine amine, an oxazolonaphthyridine amine, a thiazolonaphthyridine amine, or an imidazoquinoline amines including but not limited to 4-amino-2-ethoxymethyl-αα-dimethyl-1H-imidazo[4,5-c]quinolin-1-ethanol, 1-(2-methylpropyl)-1H-imidazo[4,5-c]quinolin-4-amine, a 1,2-bridged imidazoquinoline amine, a sulfonamido-substituted imidazoquinoline amine; a urea-substituted imidazoquinoline amine; or a heteroaryl ether-substituted imidazoquinoline amine. The IRM may induce the production of one or more cytokines including but not limited to Type I interferons.

The IRM compound may be incorporated into a composition for topical administration. Suitable types of compositions include, but are not limited to, ointments, gels, foams, creams, lotions, solutions, suspensions, emulsions, pastes, powders, soaps, surfactant-containing cleaning preparations, solid sticks (e.g., wax- or petroleum-based sticks), oils and sprays. In particular exemplary embodiments, the IRM compound may be incorporated into, for example, a sunscreen, a skin lotion, a skin moisturizer, or cosmetic.

Alternatively, the IRM compound may be incorporated into any vehicle suitable for systemic delivery. Typical systemic delivery routes include but are not limited to injection (e.g., intravenous, subcutaneous, intraperitoneal, intradermal), inhalation, ingestion, transdermal, or transmucosal delivery.

The particular amount of IRM compound necessary to (1) prophylactically reduce or prevent, or (2) therapeutically treat UV-induced immunosuppression in a subject may depend, at least in part, on one or more factors. Such factors include but are not limited to the particular IRM compound being administered, the state of the subject's immune system (e.g., suppressed, compromised, stimulated); the subject's past and expected UV exposure; the route of administering the IRM; and the desired result (i.e., prophylactic reduction or prevention, or therapeutic treatment). Accordingly it is not practical to set forth generally the amount that constitutes an effective amount of IRM compound. Those of ordinary skill in the art, however, can readily determine the appropriate amount with due consideration of such factors.

EXAMPLES

The following examples have been selected merely to further illustrate features, advantages, and other details of the invention. It is to be expressly understood, however, that while the examples serve this purpose, the particular materials and amounts used as well as other conditions and details are not to be construed in a matter that would unduly limit the scope of this invention. Unless otherwise indicated, all percentages and ratios are by weight.

Example 1

Figure 1:
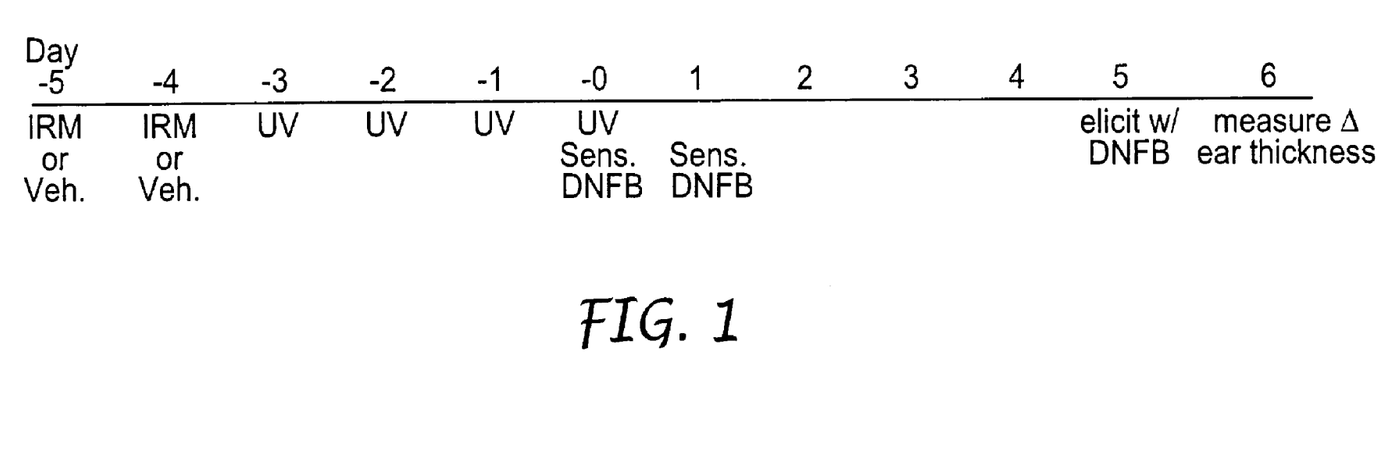
FIG. 1 is a summary of the protocol for testing the contact hypersensitivity of mice treated with IRM before exposure to UV-B radiation.

Contact Hypersensitivity in Mice Treated with IRM Before Exposure to UV-B Radiation FIG. 1 summarizes the protocol used for testing the contact hypersensitivity of mice treated with immune response modifier compound 1-(2-methylpropyl)-1H-imidazo[4,5-c]quinolin-4-amine (IRM) before exposure to UV-B radiation.

A topical cream including either a) 5% IRM (treated), or b) no IRM (vehicle-treated) was applied to a shaved portion of the abdomen of UVB-susceptible C57BL6 mice. The cream was applied for two consecutive days beginning five days before sensitization (Day −5 and Day −4).

The mice were exposed to either a) UV-B radiation, 70 mJ/cm from FS-20 light bulbs (National Biological Corp., Twinsburg, Ohio) equipped with a cellulose acetate filter to provide predominantly UV-B output, or b) sham radiation for four consecutive days beginning at three days prior to sensitization (Day −3 through Day 0).

The mice were sensitized for two consecutive days beginning at Day 0 (Day 0 and Day 1) with 25 μL of 0.5% dinitrofluorobenzene (DNFB, Sigma Chemical Co., St. Louis, Mo.) applied to the shaved portion of the abdomen.

On Day 5 after sensitization, the mice were challenged with DNFB on the pinna of the ear.

On Day 6 after sensitization, the extent to which the thickness of the ear pinna changed was measured in both the treated and untreated mice.

Figure 2:
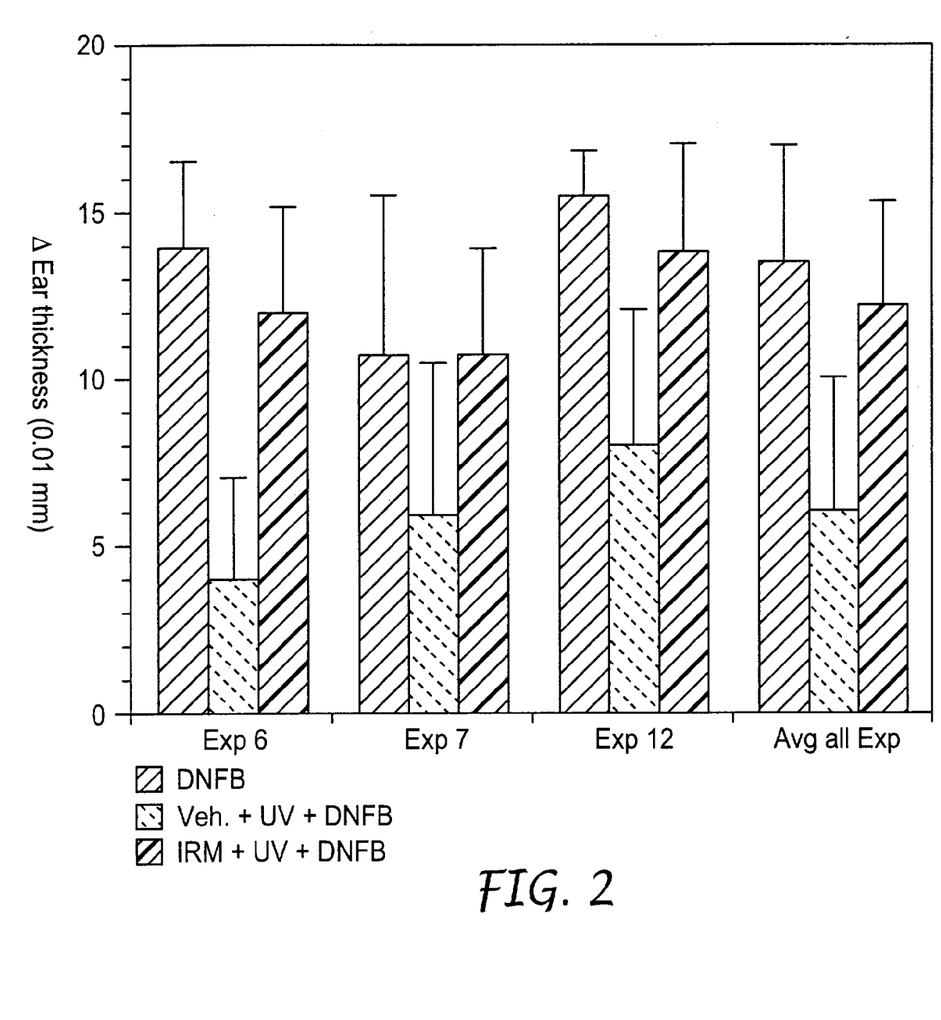
FIG. 2 is a bar graph summarizing the contact hypersensitivity of mice treated with IRM before exposure to UV-B radiation.

Three experiments were performed according to the protocol summarized in FIG. 1. The results of each of the three experiments and the average of all three experiments are provided in FIG. 2.

Example 2

Figure 3:
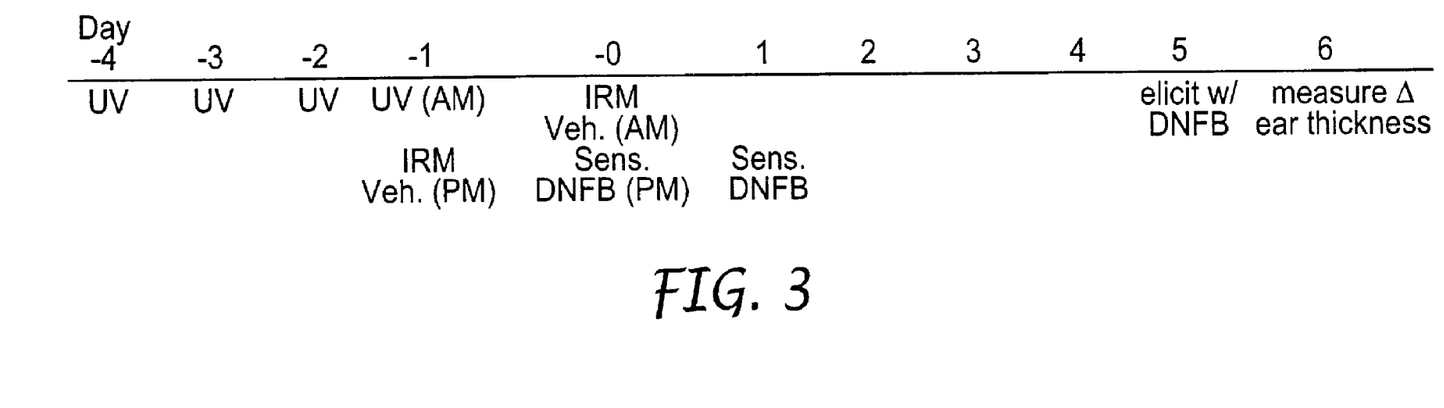
FIG. 3 is a summary of the protocol for testing the contact hypersensitivity of mice treated with IRM after exposure to UV-B radiation.

Contact Hypersensitivity in Mice Treated with IRM After Exposure to UV-B Radiation FIG. 3 summarizes the protocol used for testing the contact hypersensitivity of mice treated with immune response modifier compound 1-(2-methylpropyl)-1H-imidazo[4,5-c]quinolin-4-amine (IRM) after exposure to UV-B radiation.

The mice were exposed to either a) UV-B radiation, 70 mJ/cm from FS-20 light bulbs (National Biological Corp., Twinsburg, Ohio) equipped with a cellulose acetate filter to provide predominantly UV-B output, or b) sham radiation for four consecutive days beginning at four days prior to sensitization (Day −4 through Day −1).

A topical cream including either a) 5% IRM (treated), or b) no IRM (vehicle-treated) was applied to a shaved portion of the abdomen of UVB-susceptible C57BL6 mice. The cream was applied for two consecutive days beginning one day before sensitization (Day −1 and Day 0).

The mice were sensitized for two consecutive days beginning at Day 0 (Day 0 and Day 1) with 25 μL of 0.5% dinitrofluorobenzene (DNFB, Sigma Chemical Co., St. Louis, Mo.) applied to the shaved portion of the abdomen.

On Day 5 after sensitization, the mice were challenged with DNFB on the pinna of the ear.

On Day 6 after sensitization, the extent to which the thickness of the ear pinna changed was measured in both the treated and untreated mice.

Figure 4:
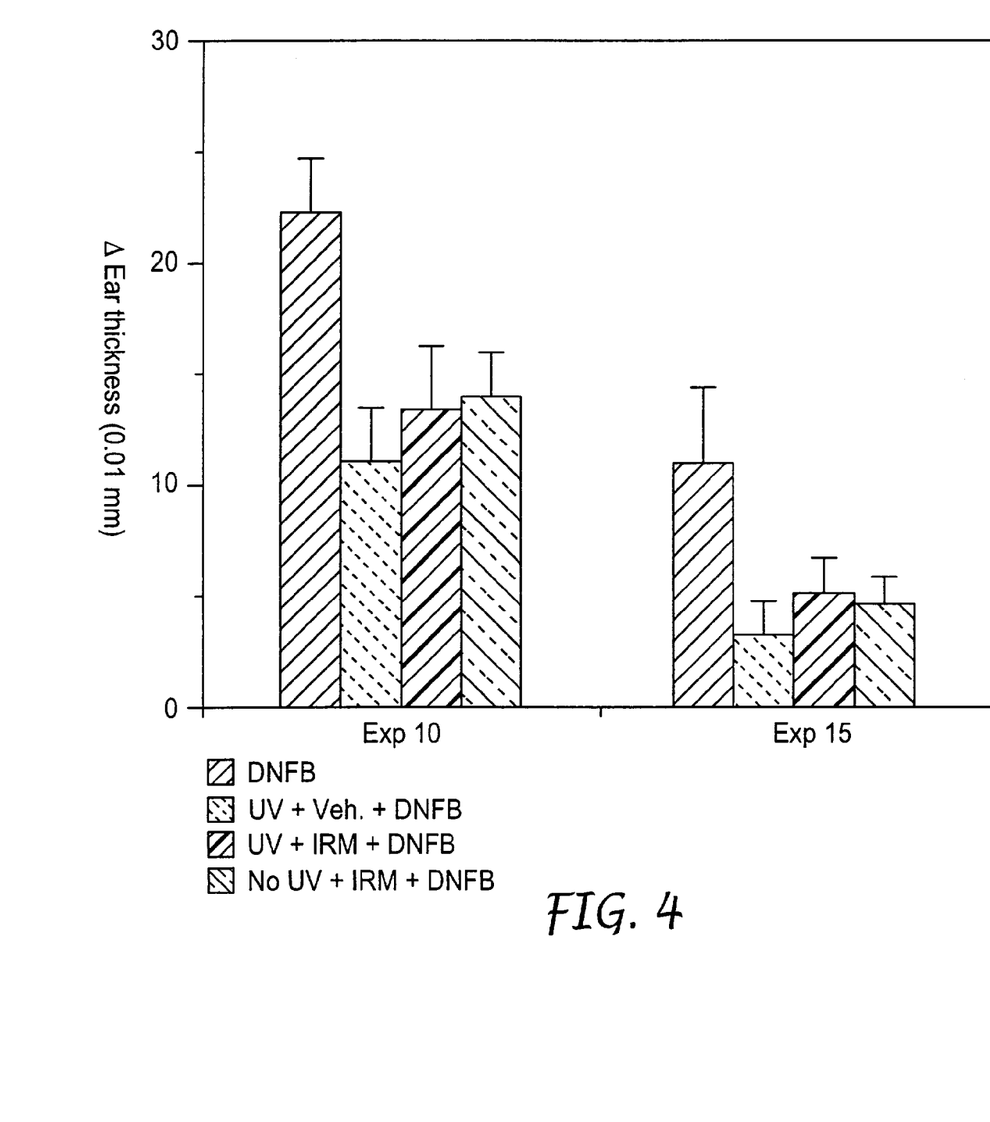
FIG. 4 is a bar graph summarizing the contact hypersensitivity of mice treated with IRM after exposure to UV-B radiation.

Two experiments were performed according to the protocol summarized in FIG. 3. The results of those two experiments are shown in FIG. 4.

The complete disclosures of the patents, patent documents and publications cited herein are incorporated by reference in their entirety as if each were individually incorporated. In case of conflict, the present specification shall control.

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A method of reducing UV-induced immunosuppression comprising administering to a treatment area an immune response modifier compound in an amount effective to inhibit UV-induced immunosuppression,
wherein to immune response modifier compound is selected from the group consisting of an imidazoquinoline amine, an imidazopyridine amine, a 6,7-fused cycloalkylimidazopyridine amine, a 1,2-bridged imidazoquinoline amine, an imidazonaphthyridine amine, an imidazotetrahydronaphthyridine amine, an oxazoloquinoline amine, a thiazoloquinoline amine, an oxazolopyridine amine, a thiazolopyridine amine, an oxazolonaphthyridine amine, a thiazolonaphthyridine amine, and a CpG oligonucleotide.

2. The method of claim 1 wherein administration of to immune response modifier compound occurs prior to exposure of the treatment area to UV irradiation.

3. The method of claim 1 wherein the immune response modifier compound is an agonist of at least one Toll-like receptor (TLR).

4. The method of claim 3 wherein to immune response modifier compound is an agonist of TLR7, TLR8, or TLR9.

5. The method of claim 1 wherein the immune response modifier compound is selected from the group consisting of an imidazoquinoline amine, an imidazopyridine amine, a 6,7-fused cycloalkylimidazopyridine amine, a 1,2-bridged imidazoquinoline amine, an imidazonaphthyridine amine, an imidazotetrahydronaphthyridine amine, an oxazoloquinoline amine, a thiazoloquinoline amine, an oxazolopyridine amine, a thiazolopyridine amine, an oxazolonaphthyridine amine, amine, a thiazolonaphthyridine amine.

6. The method of claim 6 wherein the immune response modifier compound is administered via a topical application vehicle.

7. The method of claim 6 wherein the topical application vehicle comprises a cream, a gel, a spray, an ointment, a lotion, a solution, a suspension, an emulsion, a paste, a powder, or an oil.

8. The method of claim 6 wherein the immune response modifier compound is administered via a sunscreen, a skin lotion, a skin moisturizer, a cosmetic, a soap, a spray, a foam, a gel, or a surfactant-containing cleaning preparation.

9. A method of treating UV-induced immunosuppression comprising administering to a treatment area an immune response modifier in an amount effective to inhibit UV-induced immnunosuppression,
wherein the immune response modifier compound is selected from the group consisting of an imidazoquinoline amine, an imidazopyridine amine, a 6,7-fused cycloalkylimidazopyridine amine, a 1,2-bridged imidazoquinoline amine, an imidazonaphthyridine amine, an imidazotetrahydronaphthyridine amine, an oxazoloquinoline amine, a thiazoloquinoline amine, an oxazolopyridine amine, a thiazolopyridine amine, an oxazolonaphthyridine amine, a thiazolonaphthyridine amine, and a CpG oligonucleotide.

10. The method of claim 9 wherein administration of the immune response modifier compound occurs prior to exposure of the treatment area to UV irradiation.

11. The method of claim 9 wherein the immune response modifier compound is an agonist of at least one TLR.

12. The method of claim 11 wherein the immune response modifier compound is an agonist of TLR7, TLR8, or TLR9.

13. The method of claim 9 wherein the immune response modifier compound is selected from the group consisting of an imidazoquinoline amine, an imidazopyridine amine, a 6,7-fused cycloalkylimidazopyridine amine, a 1,2-bridged imidazoquinoline amine, an imidazonaphthyridine amine, an imidazotetrahydronaphthyridine amine, an oxazoloquinoline amine, a thiazoloquinoline amine, an oxazolopyridine amine, a thiazolopyridine amine, an oxazolonaphthyridine amine, and a thiazolonaphthyridine amine.

14. The method of claim 9 wherein the immune response modifier compound is administered via a topical application vehicle.

15. The method of claim 14 wherein the topical application vehicle comprises a cream, a gel, a spray, an ointment, a lotion, a solution, a suspension, an emulsion, a paste, a powder, or an oil.

16. The method of claim 14 wherein the immune response modifier compound is administered via a sunscreen, a skin lotion, a skin moisturizer, a cosmetic, a soap, a spray, a foam, a gel, or a surfactant-containing cleaning preparation.

* * * * *

UNITED STATES PATENT AND TRADEMARK OFFICE
CERTIFICATE OF CORRECTION

PATENT NO. : 7,030,129 B2  
APPLICATION NO. : 10/371146  
DATED : April 18, 2006  
INVENTOR(S) : Richard L. Miller It is certified that error appears in the above-identified patent and that said Letters Patent is hereby corrected as shown below:

Column 3  
Line 65, Delete "αα" and insert -- α,α -- therefor;

Column 5  
Line 65, In Claim 1 delete "to" and insert -- the -- , therefor.

Column 6  
Line 8, In Claim 2, delete "to" and insert -- the -- , therefor.

Column 6  
Line 14, In Claim 4, delete "to" and insert -- the -- therefor.

Column 6  
Line 24, In Claim 5, delete "amine," and insert -- and -- , therefor.

Column 6  
Line 26, In Claim 6, delete "claim 6" and insert -- claim 1 -- , therefor.

Signed and Sealed this

Twenty-sixth Day of December, 2006

JON W. DUDAS  
*Director of the United States Patent and Trademark Office*